US009060761B2

(12) United States Patent
Hastings et al.

(10) Patent No.: US 9,060,761 B2
(45) Date of Patent: Jun. 23, 2015

(54) CATHETER-FOCUSED MAGNETIC FIELD INDUCED RENAL NERVE ABLATION

(75) Inventors: Roger Hastings, Maple Grove, MN (US); Scott Smith, Chaska, MN (US); Leonard B. Richardson, Minneapolis, MN (US); Mark L. Jenson, Greenfield, MN (US)

(73) Assignee: BOSTON SCIENTIFIC SCIME, INC., Maple Grove, MN (US)

( * ) Notice: Subject to any disclaimer, the term of this patent is extended or adjusted under 35 U.S.C. 154(b) by 876 days.

(21) Appl. No.: 13/292,766

(22) Filed: Nov. 9, 2011

(65) Prior Publication Data
US 2012/0130362 A1 May 24, 2012

Related U.S. Application Data

(60) Provisional application No. 61/415,119, filed on Nov. 18, 2010.

(51) Int. Cl.
*A61B 18/18* (2006.01)
*A61B 18/04* (2006.01)
*A61B 18/00* (2006.01)

(52) U.S. Cl.
CPC ....... *A61B 18/04* (2013.01); *A61B 2018/00023* (2013.01); *A61B 2018/00404* (2013.01); *A61B 2018/00434* (2013.01); *A61B 2018/00511* (2013.01); *A61B 2018/00577* (2013.01)

(58) Field of Classification Search
CPC ..... A61B 18/18; A61B 18/1492; A61B 18/04
USPC ..................................... 606/33, 41
See application file for complete search history.

(56) References Cited

U.S. PATENT DOCUMENTS

| 164,184 A | 6/1875 | Kiddee |
| 1,167,014 A | 1/1916 | O'Brien |
| (Continued) | | |

FOREIGN PATENT DOCUMENTS

| DE | 10038737 A1 | 2/2002 |
| EP | 1053720 A1 | 11/2000 |
| (Continued) | | |

OTHER PUBLICATIONS

CardioVascular Technologies Inc., "Heated Balloon Device Technology," 11 pages, 2008.

(Continued)

*Primary Examiner* — Christopher D Koharski
*Assistant Examiner* — Michael Carey
(74) *Attorney, Agent, or Firm* — Seager, Tufte & Wickhem, LLC

(57) ABSTRACT

A flexible catheter includes a magnetically permeable element provided at its distal end. The magnetically permeable element is configured for placement within the renal artery. External coils, positionable on anterior and posterior portions of a patient in proximity to the renal artery, are coupled to a generator which energizes the external coils to create a high-frequency oscillating magnetic field in body tissue between the external coils including the renal artery and perivascular renal nerve tissue. The magnetically permeable element serves to concentrate the magnetic field in a region near the renal artery. The concentrated magnetic field induces high frequency electric current sufficient to ablate the perivascular renal nerve tissue proximate the renal artery. A cooling arrangement can be provided at the catheter's distal end and configured to provide cooling to the renal artery during ablation of the perivascular renal nerve tissue.

23 Claims, 7 Drawing Sheets

(56) References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |

(56) References Cited

U.S. PATENT DOCUMENTS

| | | |
|---|---|---|
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |

(56) References Cited

U.S. PATENT DOCUMENTS

| | | |
|---|---|---|
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |

(56) References Cited

U.S. PATENT DOCUMENTS

| | | |
|---|---|---|
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |

(56) References Cited

U.S. PATENT DOCUMENTS

| | | |
|---|---|---|
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |

(56) References Cited

U.S. PATENT DOCUMENTS

| | | |
|---|---|---|
| 7,348,003 B2 | 3/2008 | Salcedo et al. |
| 7,352,593 B2 | 4/2008 | Zeng et al. |
| 7,354,927 B2 | 4/2008 | Vu |
| 7,358,732 B2 | 4/2008 | Van Der Kouwe et al. |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |

(56) References Cited

U.S. PATENT DOCUMENTS

| | | |
|---|---|---|
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |

(56) References Cited

U.S. PATENT DOCUMENTS

| | | |
|---|---|---|
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1 | 6/2006 | Demarais et al. |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0269555 A1 | 11/2006 | Salcedo et al. |
| 2006/0271111 A1 | 11/2006 | Demarais et al. |
| 2006/0276852 A1 | 12/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066957 A1 | 3/2007 | Demarais et al. |
| 2007/0066972 A1 | 3/2007 | Ormsby et al. |
| 2007/0073151 A1 | 3/2007 | Lee |
| 2007/0088347 A1* | 4/2007 | Young et al. ............ 606/41 |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0203455 A1 | 8/2007 | Tremaglio, Jr. et al. |
| 2007/0203480 A1 | 8/2007 | Mody et al. |
| 2007/0203549 A1 | 8/2007 | Demarais et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |

(56) References Cited

U.S. PATENT DOCUMENTS

| | | |
|---|---|---|
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0182319 A1* | 7/2009 | Lane et al. ............. 606/21 |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221939 A1 | 9/2009 | Demarais et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0057150 A1 | 3/2010 | Demarais et al. |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0094250 A1 | 4/2010 | Gumm |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286566 A1 | 11/2010 | Griffin et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |

(56) References Cited

U.S. PATENT DOCUMENTS

| | | |
|---|---|---|
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | WO2006022790 | 3/2006 |
| WO | WO2006041881 | 4/2006 |
| WO | 2006105121 A2 | 10/2006 |
| WO | WO2007035537 | 3/2007 |
| WO | WO2007078997 | 7/2007 |
| WO | WO2007086965 | 8/2007 |
| WO | WO2007103879 | 9/2007 |
| WO | WO2007103881 | 9/2007 |
| WO | WO2007121309 | 10/2007 |
| WO | WO2007146834 | 12/2007 |
| WO | 2008014465 A2 | 1/2008 |
| WO | WO2008003058 | 1/2008 |
| WO | WO2008061150 | 5/2008 |
| WO | WO2008061152 | 5/2008 |
| WO | WO2008070413 | 6/2008 |
| WO | 2009121017 A1 | 10/2009 |
| WO | 2010067360 A2 | 6/2010 |
| WO | WO2010078175 | 7/2010 |
| WO | 2010102310 A2 | 9/2010 |
| WO | WO2010129661 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | WO2011091069 | 7/2011 |

(56) References Cited

FOREIGN PATENT DOCUMENTS

| WO | 2011130534 A2 | 10/2011 |
| WO | WO2011130005 | 10/2011 |
| WO | WO2011139589 | 11/2011 |
| WO | 2012019156 A1 | 2/2012 |
| WO | WO2012019156 | 2/2012 |
| WO | 2013049601 A2 | 4/2013 |

OTHER PUBLICATIONS

Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," Med Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries in Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, an Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.

(56) References Cited

OTHER PUBLICATIONS

Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.

Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.

Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.

Popma et al., "Percutaneous Coronary and Valvular Intervention," p. 1364-1405.

Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.

Romer et al., "Histopathology of Human Coronary Atherosclerosis by Quantifying Its Chemical Composition With Raman Spectroscopy," Circulation, 1998, p. 878-885, vol. 97.

Schauerte et al., "Catheter Ablation of Cardiac Autonomic Nerves for Prevention of Vagal Atrial Fibrillation," Circulation, 2000, p. 2774-2780, vol. 102.

Scheller et al., "Intracoronary Paclitaxel Added to Contrast Media Inhibits In-Stent Restenosis of Porcine Coronary Arteries," American Heart Association, 2002, p. 2227.

Scheller et al., "Potential solutions to the current problem: coated balloon," EuroIntervention, 2008, p. C63-C66, vol. 4 (Supplement C).

Shaffer, "Scientific basis of laser energy," Clinics in Sports Medicine, 2002, p. 585-598, vol. 21.

Shmatukha et al., "MRI temperature mapping during thermal balloon angioplasty," Physics in Medicine and Biology, 2006, p. N163-N171, vol. 51.

Slager et al., "Vaporization of Atherosclerotic Plaques by Spark Erosion," J Am Coll Cardiol, 1985, p. 21-25.

Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.

Suselbeck et al., "In vivo intravascular electric impedance spectroscopy using a new catheter with integrated microelectrodes," Basic Res Cardiol, 2005, p. 28-34, vol. 100.

Suselbeck et al., "Intravascular electric impedance spectroscopy of atherosclerotic lesions using a new impedance catheter system," Basic Res Cardiol, 2005, p. 446-452, vol. 100.

Tepe et al., "Local Delivery of Paclitaxel to Inhibit Restenosis during Angioplasty of the Leg," The New England Journal of Medicine, 2008, p. 689-699, vol. 358.

US 8,398,630, 03/2013, Demarais et al. (withdrawn)

* cited by examiner

CATHETER-FOCUSED MAGNETIC FIELD INDUCED RENAL NERVE ABLATION

RELATED PATENT DOCUMENTS

This application claims the benefit of Provisional Patent Application Ser. No. 61/415,119 filed Nov. 18, 2010, to which priority is claimed pursuant to 35 U.S.C. §119(e) and which is incorporated herein by reference.

SUMMARY

Embodiments of the disclosure are directed to apparatuses and methods for ablating target tissue of the body using a concentrated magnetic field to induce high frequency electric current sufficient to ablate the target tissue. According to various embodiments, an apparatus includes a flexible elongated member having a proximal end, a distal end, and a length sufficient to access a target vessel of the body relative to a percutaneous access location. A magnetically permeable element is provided at a distal end of the elongated member. The magnetically permeable element has poor electrical conductivity and is configured for placement within the target vessel and adjacent a wall of the target vessel. One or more external coils are positionable on one or both of anterior and posterior portions of a patient in proximity to the target vessel. A generator is coupled to the external coils and configured to energize the external coils to create a high-frequency oscillating magnetic field in body tissue between the external coils including the target vessel and target tissue proximate the target vessel. The magnetically permeable element serves to concentrate the magnetic field in a region near the target vessel. The concentrated magnetic field induces high frequency electric current sufficient to ablate the target tissue proximate the vessel.

According to some embodiments, an apparatus includes a flexible elongated member having a proximal end, a distal end, and a length sufficient to access a renal artery relative to a percutaneous access location. A magnetically permeable element is provided at a distal end of the elongated member. The magnetically permeable element has poor electrical conductivity and is configured for placement within the renal artery and adjacent a wall of the renal artery. One or more external coils are positionable on one or both of anterior and posterior portions of a patient in proximity to the renal artery. A generator is coupled to the external coils and configured to energize the external coils to create a high-frequency oscillating magnetic field in body tissue between the external coils including the renal artery and perivascular renal nerve tissue proximate the renal artery. The magnetically permeable element serves to concentrate the magnetic field in a region near the renal artery. The concentrated magnetic field induces high frequency electric current sufficient to ablate the perivascular renal nerve tissue proximate the renal artery. A cooling arrangement can be provided at the distal end of the elongated member and configured to provide cooling to the renal artery during ablation of the perivascular renal nerve tissue.

In other embodiments, a method involves energizing one or more external coils positionable on one or both of anterior and posterior portions of a patient in proximity to a renal artery to create a high-frequency oscillating magnetic field in body tissue between the external coils including renal artery tissue and perivascular renal nerve tissue adjacent the renal artery. The method also involves concentrating the magnetic field in a region near the renal artery, and ablating the perivascular renal nerve tissue using high frequency electric current induced in the perivascular renal nerve tissue by the concentrated magnetic field. The method may further involve providing cooling to the renal artery during ablation of the perivascular renal nerve tissue.

These and other features can be understood in view of the following detailed discussion and the accompanying drawings.

DETAILED DESCRIPTION

Figure 1:
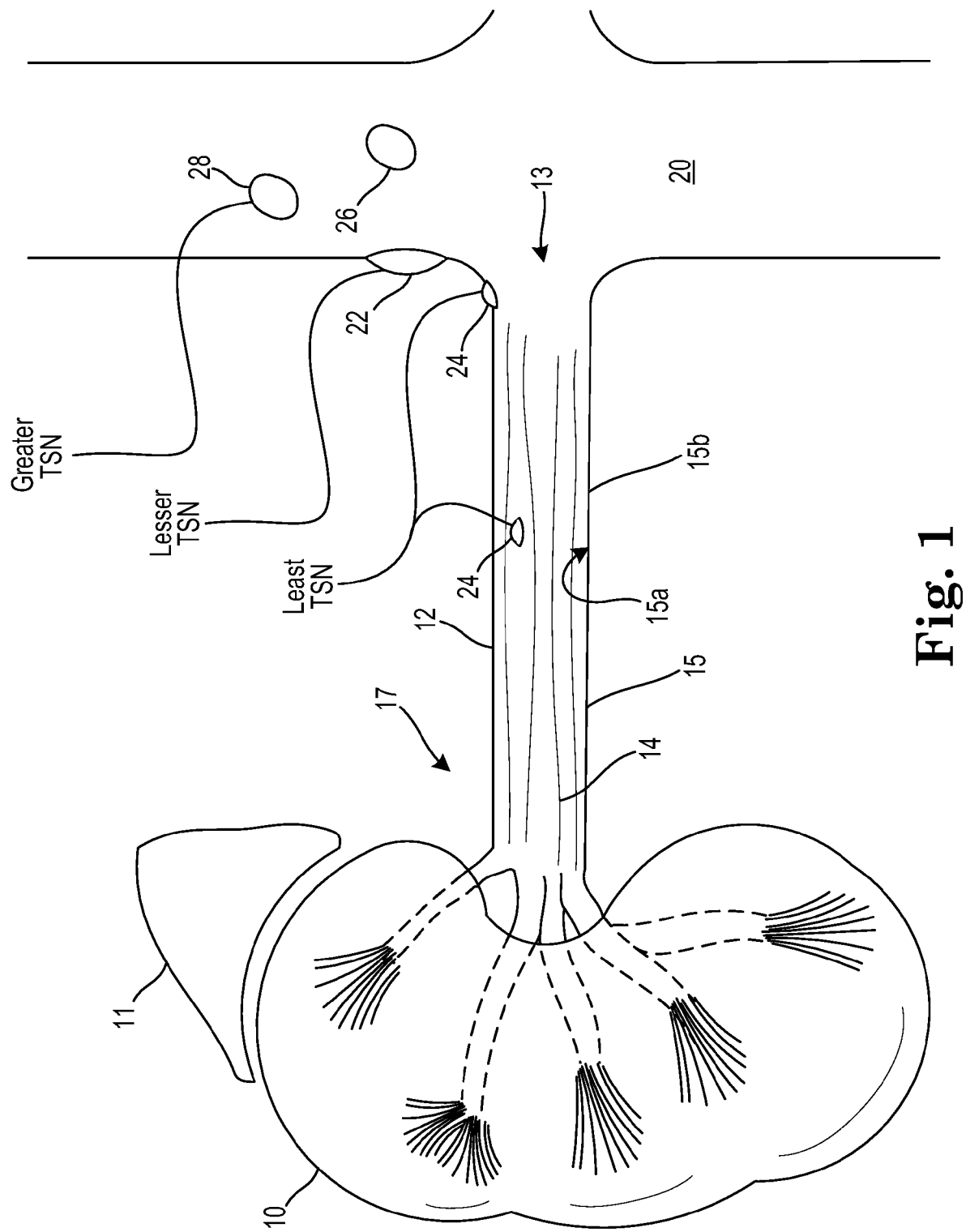
FIG. 1 is an illustration of a right kidney and renal vasculature including a renal artery branching laterally from the abdominal aorta.

Ablation of perivascular renal nerves has been used as a treatment for hypertension. Radiofrequency (RF) electrodes placed in the renal artery can be used to ablate the nerves, but with risk of artery wall injury. To control injury to the artery wall, one approach is to ablate at discrete locations along and around the artery, repositioning the electrode between locations. Devices with multiple RF electrodes have been proposed to avoid the need for multiple repositioning and ablation cycles, but these devices and their use are more complicated.

Even with ablation of discrete locations, renal artery injury in these locations can occur due to local high temperatures resulting from high current density near the electrodes. Many RF ablation approaches produce a small focal area of heating, with the greatest heating at the artery wall. Away from the electrode, the current density and ohmic heating fall off very rapidly. In order to effectively ablate the target tissue, a larger zone of heating, or multiple separate ablations at different locations, is needed.

Embodiments of the disclosure are directed to apparatuses and methods for effectively ablating target tissue of the body with reduced injury to non-targeted tissue. Embodiments of the disclosure are directed to apparatuses and methods for ablation of perivascular renal nerves for treatment of hypertension. Embodiments are directed to apparatuses and methods for generating a high-frequency oscillating magnetic field in body tissue that includes target tissue to be ablated, concentrating the magnetic field in a region near a magnetically permeable element positioned proximate the target tissue, and ablating the target tissue using high frequency electric current induced in the target tissue proximate the magnetically permeable element by the concentrated magnetic field. In some embodiments, the magnetically permeable element is configured for placement within a vessel, such as the renal artery, and the target tissue is located proximate the vessel, such as perivascular renal nerve tissue adjacent the renal artery.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arterioles, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arterioles and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

Figure 2A:
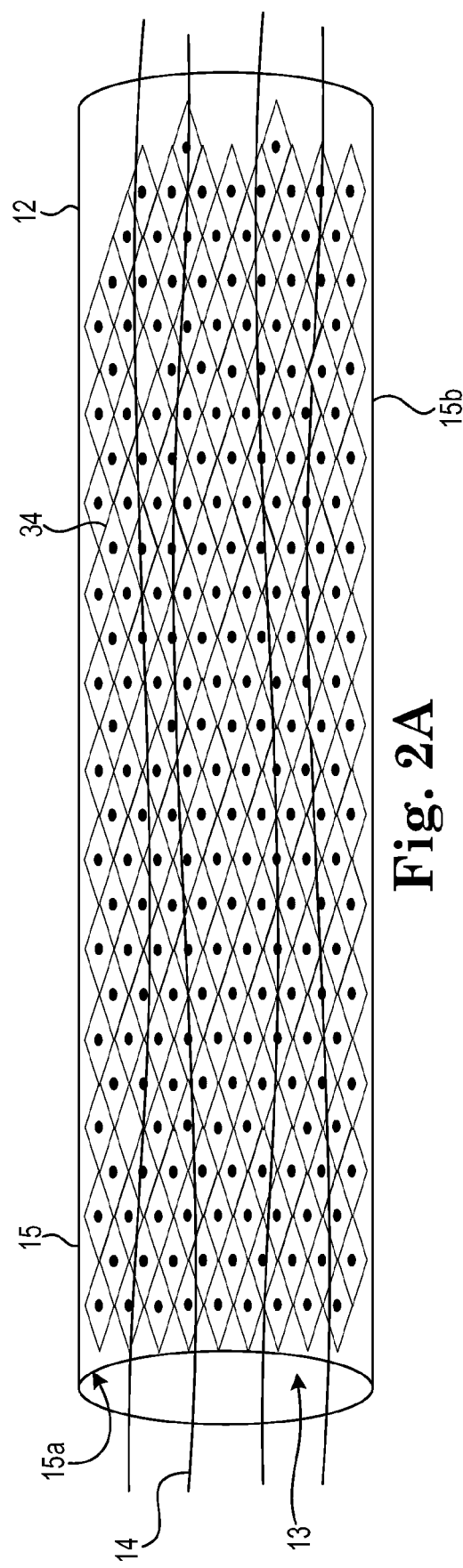
FIGS. 2A and 2B illustrate sympathetic innervation of the renal artery.
Figure 2B:
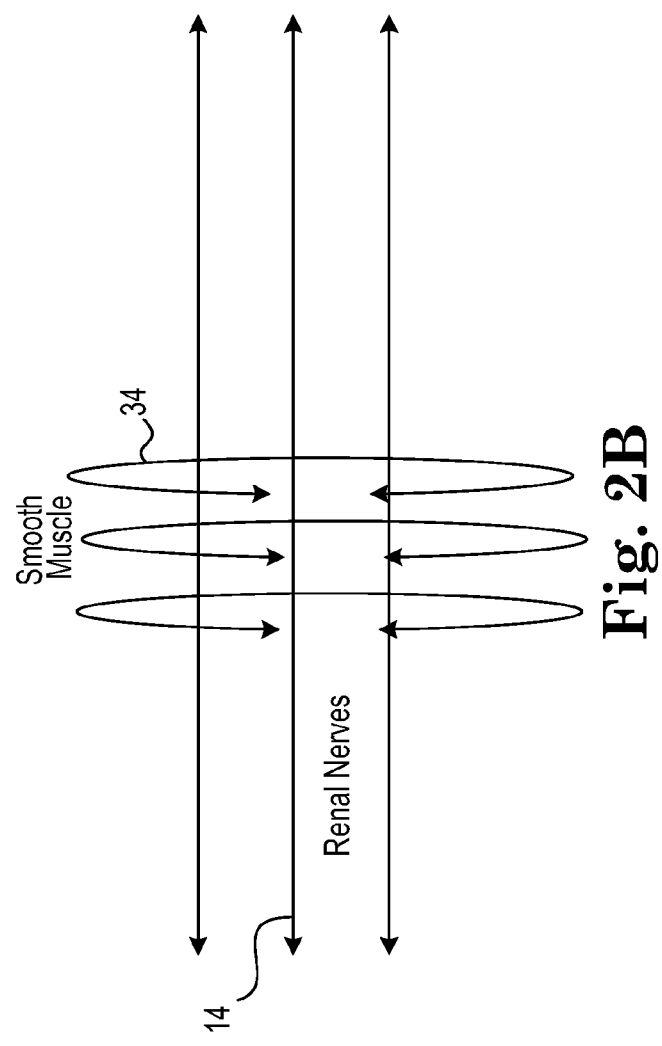

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arterioles of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
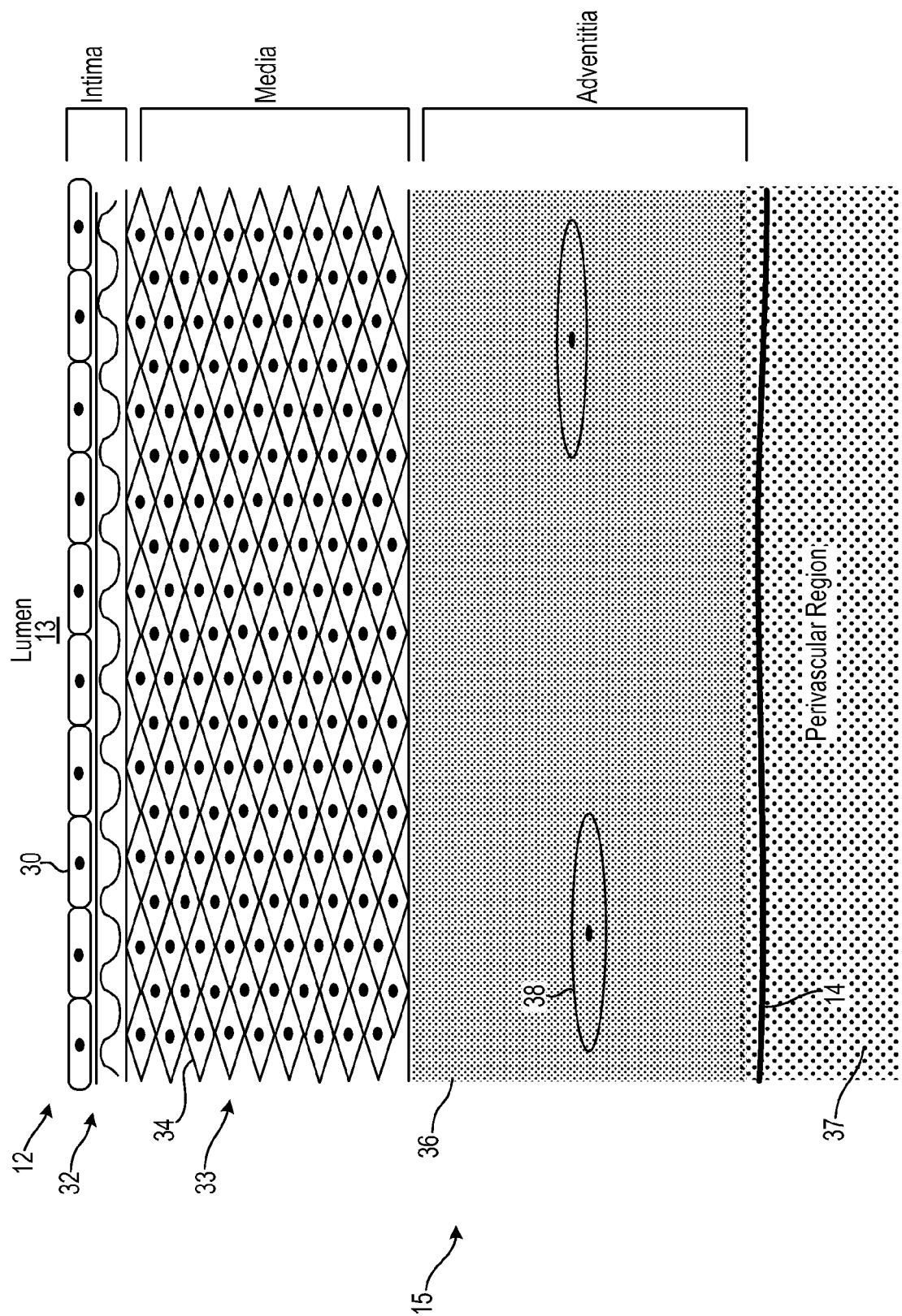
FIG. 3A illustrates various tissue layers of the wall of the renal artery.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3B:
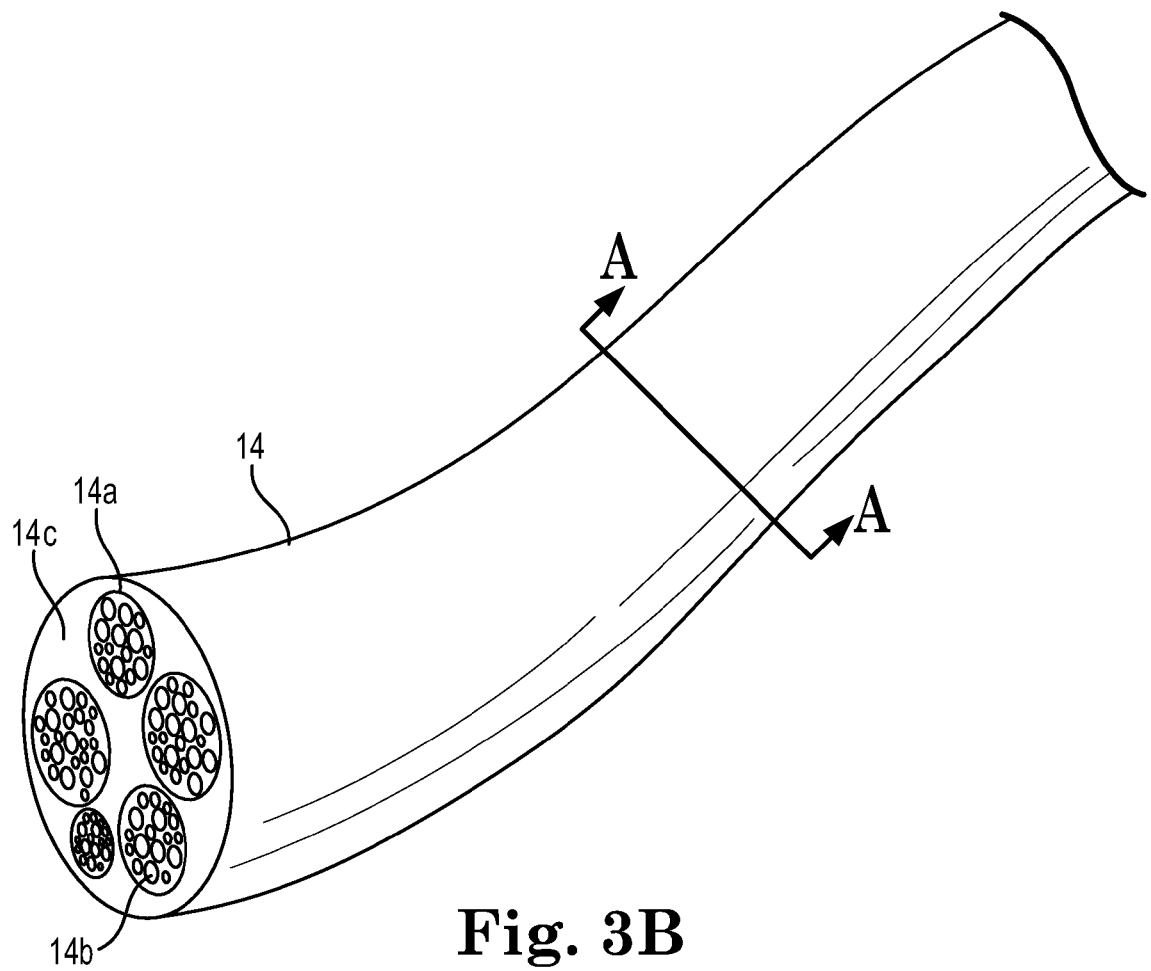
FIGS. 3B and 3C illustrate a portion of a renal nerve.
Figure 3C:
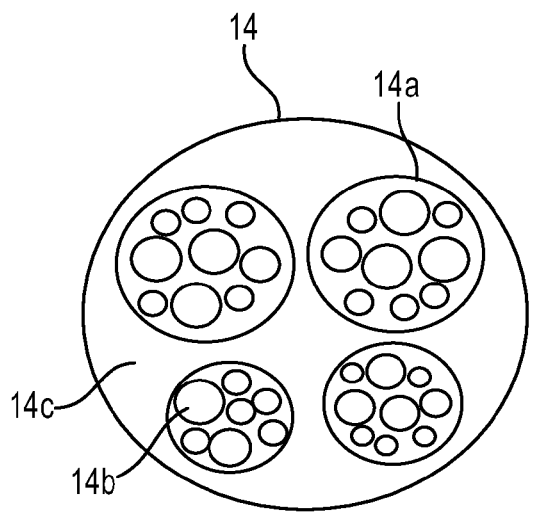

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In preferred embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may be implemented to deliver a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may be implemented to deliver a denervation therapy that interrupts conduction of nerve impulses along the renal nerve fibers 14b by imparting damage to the renal nerve fibers 14b consistent with neruapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a treatment apparatus according to embodiments of the disclosure.

A treatment apparatus may be implemented to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b is preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

A treatment apparatus may be implemented to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Figure 4:
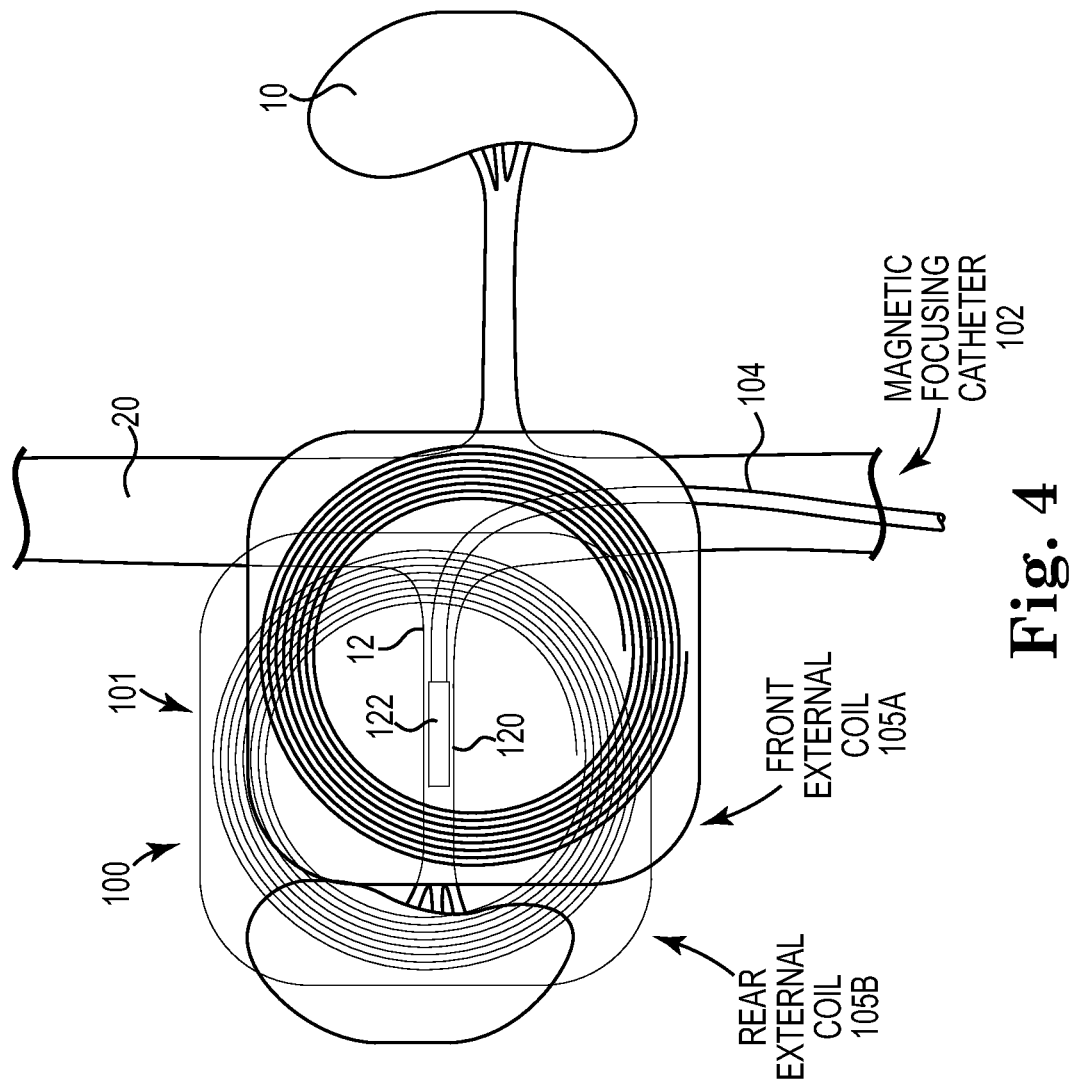
FIG. 4 illustrates a medical system for ablating target tissue of the body, such as perivascular renal nerve tissue, using a concentrated magnetic field to induce high frequency electric current sufficient to ablate the target tissue in accordance with various embodiments.

In accordance with various embodiments, and with reference to FIG. 4, there is shown an apparatus 100 for ablating target tissue of the body. The apparatus 100 shown in FIG. 4 includes an external apparatus 101 and an apparatus 102 configured for placement within the body. The external and internal apparatuses 101 and 102 cooperate to focus an externally generated magnetic field at a target region within the body and intensify the magnetic field near the target region resulting in increased induced electric current and ohmic heating in target tissue within or near the target region. The ohmic heating is preferably controlled so that the target tissue is thermally ablated, but non-targeted tissue is only negligibly affected.

As discussed previously above, conventional RF ablation approaches produce a small focal area of heating, with the greatest heating at the artery. The current density and ohmic heating fall off by the $4^{th}$ power of the distance from the electrode center. Embodiments of the disclosure are directed to approaches that generate a more uniform heating in the region adjacent to the artery, allowing more complete ablation of target tissue with less artery wall injury.

According to the embodiment shown in FIG. 4, the internal apparatus 102 includes a flexible elongated member 104 having a proximal end, a distal end, and a length sufficient to access a target vessel of the body, such as a renal artery 12, relative to a percutaneous access location. A magnetically permeable element 120 is provided at a distal end of the elongated member 104. The magnetically permeable element 120 preferably has low or poor electrical conductivity and is configured for placement within the renal artery 12 and adjacent a wall of the artery 12. The internal apparatus 102 shown in FIG. 4 is preferably delivered to the renal artery 12 via the inferior aorta 20 using one or both of a guiding catheter and a delivery sheath. Alternatively, the internal apparatus 102 can be implemented as a guiding catheter, and may incorporate a lumen through which a guidewire can pass for advancing the apparatus 102 through vasculature via an over-the-wire delivery technique, for example. Marker bands or features can be placed on one or multiple parts of the elongated member 104, the magnetically permeable element 120, and/or a support arrangement 122 that contains or supports the magnetically permeable element 120. The marker bands or features aid the clinician in determining the location and position of specific portions of the elongated member 104, such as the magnetically permeable element 120.

The external apparatus 101 includes one or more external coils 105A and 105B that can be positioned on one or both of anterior and posterior portions of a patient in proximity to the renal artery 12. The external apparatus 101 further includes a generator (shown in FIG. 6) coupled to the external coils 105A and 105B. The generator is configured to energize the external coils 105A and 105B to create a high-frequency oscillating magnetic field in body tissue between the external coils 105A and 105B including the renal artery 12 and perivascular renal nerve tissue proximate the renal artery 12. The magnetically permeable element 120 serves to concentrate the magnetic field in a region near the renal artery 12. The concentrated magnetic field induces high frequency electric current sufficient to ablate the perivascular renal nerve tissue proximate the renal artery 12.

The internal apparatus 102 may include a support arrangement 122 at the distal end of the elongated member 104. The support member 122 preferably provides support for, or containment of, magnetic material of the magnetically permeable element 120. The magnetically permeable element 120 may, for example, incorporate a vessel 122 filled with fluid comprising magnetic material. The magnetically permeable element 120 may incorporate a balloon 122 configured to receive a fluid comprising magnetic material from a lumen arrangement of the elongated member 104. The magnetically permeable element 120 can incorporate a balloon 122 formed from a composite polymeric material comprising magnetic material or a polymeric balloon 122 comprising a coating of nonconductive or poorly conductive magnetic material. The magnetically permeable element 120 may incorporate a balloon 122, and at least a circumferential region of the balloon 122 is heated by the induced electric current, such that a complete circumferential region of the perivascular renal nerve tissue is ablated. The magnetically permeable element 120 may include a solid element or a coated element 120 comprising nonconductive or poorly conductive magnetic material. The magnetically permeable element 120 can incorporate a tube 122 containing magnetic material. Other configurations of the magnetically permeable element 120 and support arrangement 122 are contemplated.

Figure 5:
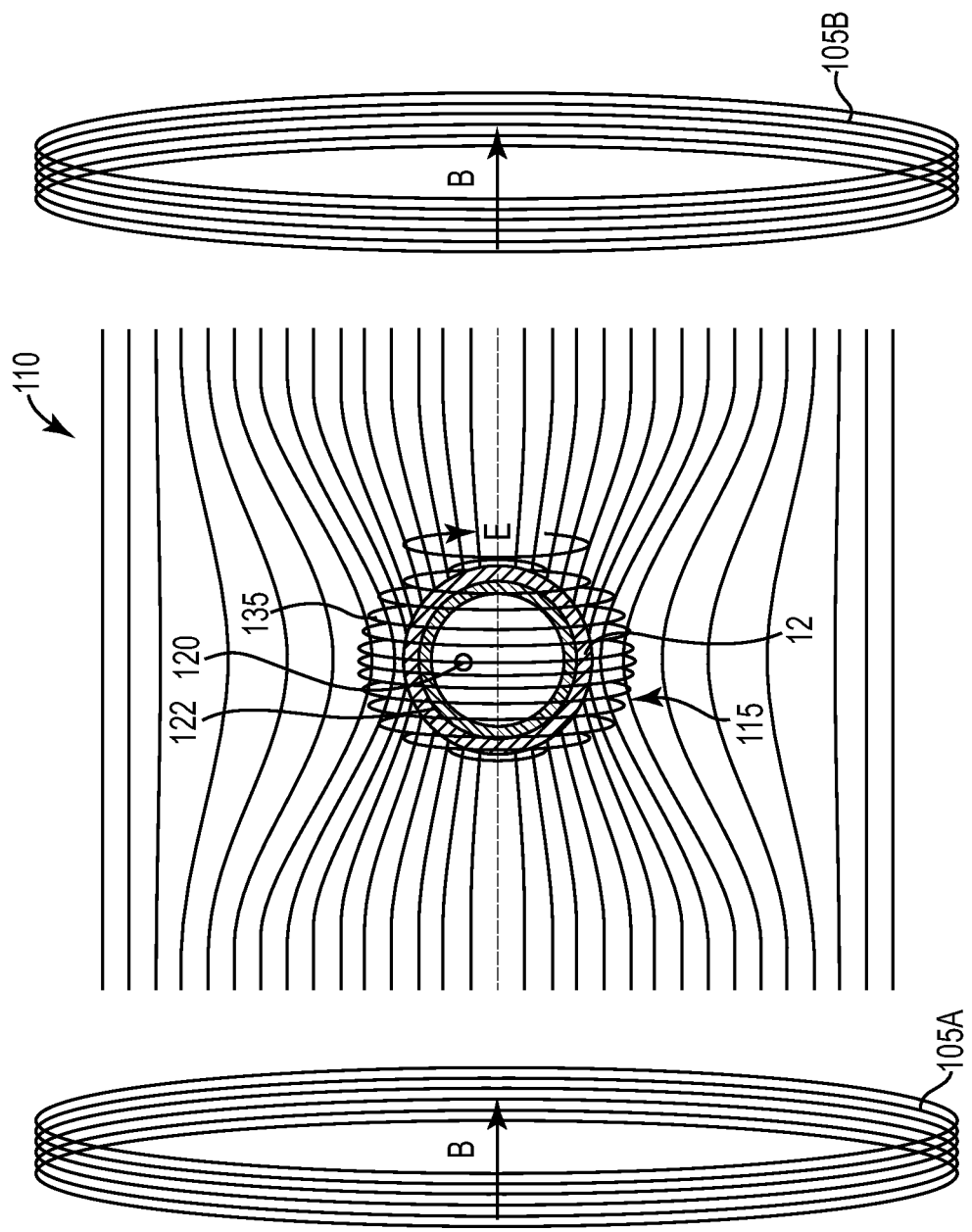
FIG. 5 is a schematic representation of an externally generated magnetic field concentrated at a target region adjacent a renal artery by use of a magnetic focusing catheter in accordance with various embodiments.

Referring now to FIG. 5, there is illustrated a schematic representation of an externally generated magnetic field 110 which is being concentrated at a target region of the body adjacent a renal artery 12 by use of a magnetic focusing catheter 102 according to various embodiments of the disclosure. FIG. 5 shows a cross-section of the renal artery 12 within which a spherical vessel 122 containing a ferrofluid 120 is positioned. In FIG. 5, the renal artery 12 is oriented coming out of the page. The electric field lines 135 around the spherical vessel 122 containing the ferrofluid 120 are illustrated for simplicity. The spherical vessel 122 that contains a ferrofluid 120 represents one of many possible configurations of a magnetically permeable element 120 and support arrangement 122, and is shown for non-limiting illustrative purposes. For example, a cylindrical or annular ferrofluid volume may be provided at a distal end or tip of a catheter shaft 104, with the current loops displaced to the side since the ferrofluid is nonconductive. In FIG. 5, the magnetic field 110 is illustrated as being concentrated by a factor of about 2 for clarity of illustration. However, concentration of the magnetic field 115 proximate the ferrofluid filled vessel 122 by ratios of magnetic permeability in the range of about 5 to 15 are typically achieved.

With reference to FIGS. 4 and 5, and in accordance with various embodiments, a balloon catheter 102 is placed in a renal artery 12 and the balloon 122 is filled with a ferrofluid 120. External coils 105A and 105B are placed on the front and the back of the patient and energized to create a high-frequency oscillating magnetic field 110 in the tissue between the coils 105A and 105B. The ferrofluid 120 concentrates the magnetic field 115 in the region near the catheter balloon 122 preferably by approximately a factor of 10. The changing magnetic field 115 induces a corresponding electric field 135 and results in high frequency electric current in the tissues adjacent the balloon 122. The current causes local resistive heating in the tissue, proportional to the square of the current, resulting in local heating near the balloon 122 approximately 100 times that resulting in the other areas of tissue subject to the magnetic field 110.

In this representative embodiment, tissue around the entire circumference of the balloon 122 is heated by the induced current, avoiding the need for repeated catheter positioning and activation as with typical RF devices. The magnetically induced heating is also more uniform, since the current is affected primarily by the local magnetic field strength, which can fall off relatively slowly with separation from a magnetically permeable balloon 122. More uniform heating in the region adjacent to the renal artery 12 is achieved, allowing more complete ablation of perivascular renal nerve tissue with less artery wall injury.

The following comparison between conventional RF catheter approaches and ablation approaches consistent with embodiments of the disclosure is provided below for illustrative purposes. Conventional RF catheter approaches involve pressing a tip electrode against the arterial tissue and application of a given dose of RF power. Ablation current flows into the arterial tissue from a portion of the tip electrode. The impedance between the tip electrode and ground pad consists of contact resistance, tissue resistance, and tissue capacitance. To estimate some ablation parameters, consider a simplified model of the RF ablation. The ablation tip can be modeled as a spherical electrode surrounded by tissue having uniform electrical resistivity. It is assumed for illustrative purposes that about ⅓ of the current passes into the arterial wall, while the remaining current is lost to the blood. The voltage at a point in arterial tissue a distance "r" from the spherical tip electrode is given by:

$$V=V_0(r_0/r) \quad (1)$$

where
V=voltage at distance r in volts
$V_0$=voltage applied to tip electrode, volts
$r_0$=tip electrode radius, meters
r=distance from center of tip electrode to point in tissue, in meters The electric field developed in the tissue is given by:

$$E=dV/dr=-V_0(r_0/r^2) \quad (2)$$

where the electric field is directed radial outward from the tip electrode. The current density is then given by Ohms law:

$$J=E/\rho=V_0(r_0/\rho r^2) \quad (3)$$

where
J=current density in Amps/m²
ρ=resistivity in Ohm-m

The total power dissipated in the arterial wall is given by:

$$P_w=\int d^3r JE \quad (4)$$

where
$P_w$=power dissipated in artery wall in Watts
$\int d^3r$=integral over the tissue volume To estimate the power dissipated in the arterial wall, an estimate is made that about ⅓ of the tip electrode area is against the artery wall, so the result is about one third of the integration over all of space. Since the integrand falls off with the inverse fourth power of distance, most of the heat is dissipated close to the electrode, and the integration can be extended over all space with the result approximately equal to the heat dissipated in tissue near the tip electrode. Substituting Equation (2) and (3) into Equation (4) above, and carrying out the integration yields:

$$P_w=(4\pi r_0/6\rho)V_0^2 \quad (5)$$

where a factor of three reduction is included to account for the arterial wall contacting one third of the tip electrode area, and a factor of two reduction is included to account for RMS value of the sine wave, RF current.

The resistivity of muscle and blood are similar, about 2 Ohm-m. The tip electrode for renal nerve ablation has a diameter of about 1.5 mm. The nominal voltage amplitude during an RF ablation is about 40 volts (varies with tissue impedance for constant power ablations). Using these values in Equation (5) above yields $P_w$=1.3 Watts. This means that 2.6 Watts is dissipated in blood. The constant power setting in the RF ablation is 8 Watts. Thus, about half of this power, or 4.1 Watts, is dissipated in the leads and contact resistance between the tip electrode and tissue.

In accordance with embodiments of the disclosure, ablative heating of innervated renal arterial and perivascular tissue is provided from currents induced by an external magnetic field 110. In accordance with the representative geometry schematically illustrated in FIG. 5, a voltage is induced in tissue adjacent the magnetically permeable ferrofluid given by:

$$V=d\Phi/dt=\omega\mu B_0 A \quad (6)$$

where
V induced voltage in volts
Φ=magnetic flux in webers
ω=2πf, where f is the frequency of the sine wave applied magnetic field in Hz
μ=magnetic permeability of the ferrofluid
$B_0$=amplitude of the applied field in Tesla
A=area of a surface near the balloon To simplify the calculation, consider currents induced to flow around the circumference of a circle of diameter "d" that lies in the plane perpendicular to the applied magnetic field 110 of FIG. 5, with the plane of the circle near the ferrofluid 120. The voltage induced around this circle is given by Equation (7) below as follows:

$$V=(\pi^2/2)\mu f B_0 d^2 \quad (7)$$

The resistance around the circular path of tissues lying within a circle of diameter "d" is estimated by a circular current path with length equal to the circumference at half of the circle radius, or πd/2, and an area equal to the radius of the circle times the width, w, of the conductive tissue, or $$R=\pi\rho/w \quad (8)$$

The heat generated in the tissue due to the induced currents is then given by:

$$P=V^2/2R=[(\pi^2/2)\mu f B_0 d^2]^2 w/2\pi\rho \quad (9)$$

Using the estimate from the RF ablation analysis below Equation (5) that the Ohmic power needed to ablate the tissue is 1.3 Watts, and taking the diameter of the circle equal to the width of the tissue ablated and both equal to 4 mm (as estimates of the tissue volume ablated in renal nerve RF ablation, taken from Haines, Biophysics of Radiofrequency Lesion Formation, Ch. 1, FIGS. 1-2), then solving Equation (9) above for μ f $B_0$ gives:

$$\mu f B_0 = 8 \times 10^5 \quad (10)$$

The permeability generally decreases with increasing frequency. As an estimate of this product, it is assumed that μ=10 at f=500 kHz can be achieved. In this case, the amplitude of the applied magnetic field needed for ablation by the induced currents is on the order of 0.15 Tesla. This is a large, but achievable magnetic field using water cooled coils 105A and 105B, for example. Coils 105A and 105B may be placed both above and below the patient over the approximate location of the renal artery 12, as shown in FIG. 4.

Tissue that is in the magnetic field but not adjacent the ferrofluid 120 will have induced currents with μ=1 in Equation (9) above. In this illustrative example, this will result in heating at a power level that is 100 times less than the tissue adjacent the ferrofluid 120, and presumably well below the level needed to significantly raise the temperature of these tissues. Also, the mixture of conductive and non-conductive body tissues, for example fat, may greatly reduce the conductivity of adjacent tissues, and may break up or prevent closed current paths in other tissues.

The power dissipated in the tissue adjacent the ferrofluid filled balloon 122 can be estimated by Equation (9) above. The heating power increases with the square of frequency, so higher frequency is desired, provided that the permeability is adequate. Ferrofluids 120 that consist of particles having a single magnetic domain may have higher permeability at high frequencies than multi-domain particle.

The magnetic particles in the ferrofluid 120 should be physically small to avoid induction of electrical currents within the particles that would generate heat within the balloon 122. Equation (9) above shows that the heating power is proportional to the fourth power of particle diameter, so conventional ferrofluids 120 having sub-micron sized particles should not heat, even though they are much less electrically resistive than body tissues. The particles need to be coated with an electrical insulating material, and suspended in an electrically insulating solvent.

A ferrofluid 120 having a large permeability compared to body tissues is desired so that heating occurs around the ferrofluid balloon 122, but not in other body tissues. Additionally, induced electric fields 135 that are spatially uniform in non-magnetic body tissues can be created, but non-uniform near the ferrofluid 120. This may be achieved, for example, using the rotating magnetic field of a bird cage winding (e.g., MRI RF bird cage), which creates a spatially uniform rotating electric field.

Near the ferrofluid balloon 122 the magnetic field 115 is distorted, and time varying electric fields 135 appear that circulate in the tissue near the balloon 122 at the rotation rate of the applied field. Heating will occur preferentially in tissues around the balloon 122 but not in tissues away from the balloon 122. Various distortions 115 of the applied field 110 and various patterns of induced electric currents in body tissue are contemplated using both paramagnetic materials and diamagnetic materials (e.g., bismuth) in geometries that optimize heating. Solid magnetic materials may be coated onto a balloon or delivered within a tube that can be coiled up against the artery wall.

In accordance with other embodiments, a balloon 122 can be inflated with ferrofluid 120. A double balloon 122 can be used in some embodiments, with the annulus inflated with ferrofluid 120. The inner balloon can be inflated with a conventional fluid. In other embodiments, a thin non-conductive coating of magnetic material can be used. The balloon 122 or other structure (e.g., catheter shaft 104 or expandable element supported at the distal end of the catheter shaft 104) can be covered with the thin non-conductive coating of magnetic material.

In various embodiments, a balloon 122 can be constructed of magnetic nanoparticles in a polymer matrix to produce a nonconductive magnetic balloon. The balloon 122 may be cooled to prevent heating of the arterial wall adjacent the balloon 122. Cooling may be provided by blood flowing through the center of the balloon (e.g., a perfusion balloon). Other cooling mechanisms include circulating cooling fluids and application of cryogenic fluids as are known in the art. The balloon 122 may contain a temperature sensor or thermometer 127 (shown in FIG. 6), for example one or more thermocouples, to monitor the temperature adjacent the balloon 122 and provide feedback to automatically or semi-automatically control the strength of the external magnetic field 110 during ablation.

According to some embodiments, and as an alternative to a ferrofluid balloon 122, a catheter 102 tipped with a ferrite or other magnetically permeable material having low electrical conductivity may be used. The ferrite is preferably pressed against the wall of the renal artery 12, and the external magnetic field 110 is applied. A thermometer 127 can be placed adjacent the artery wall in a hole through the ferrite tip to titrate the external field. A generally uniform magnetic field 110 can be obtained from external coils 105A and 105B, or a more concentrated magnetic field can be obtained with modified external components. The magnetic material on the catheter 102 can be used to orient the external components to maximize the field strength at the target region.

Figure 6:
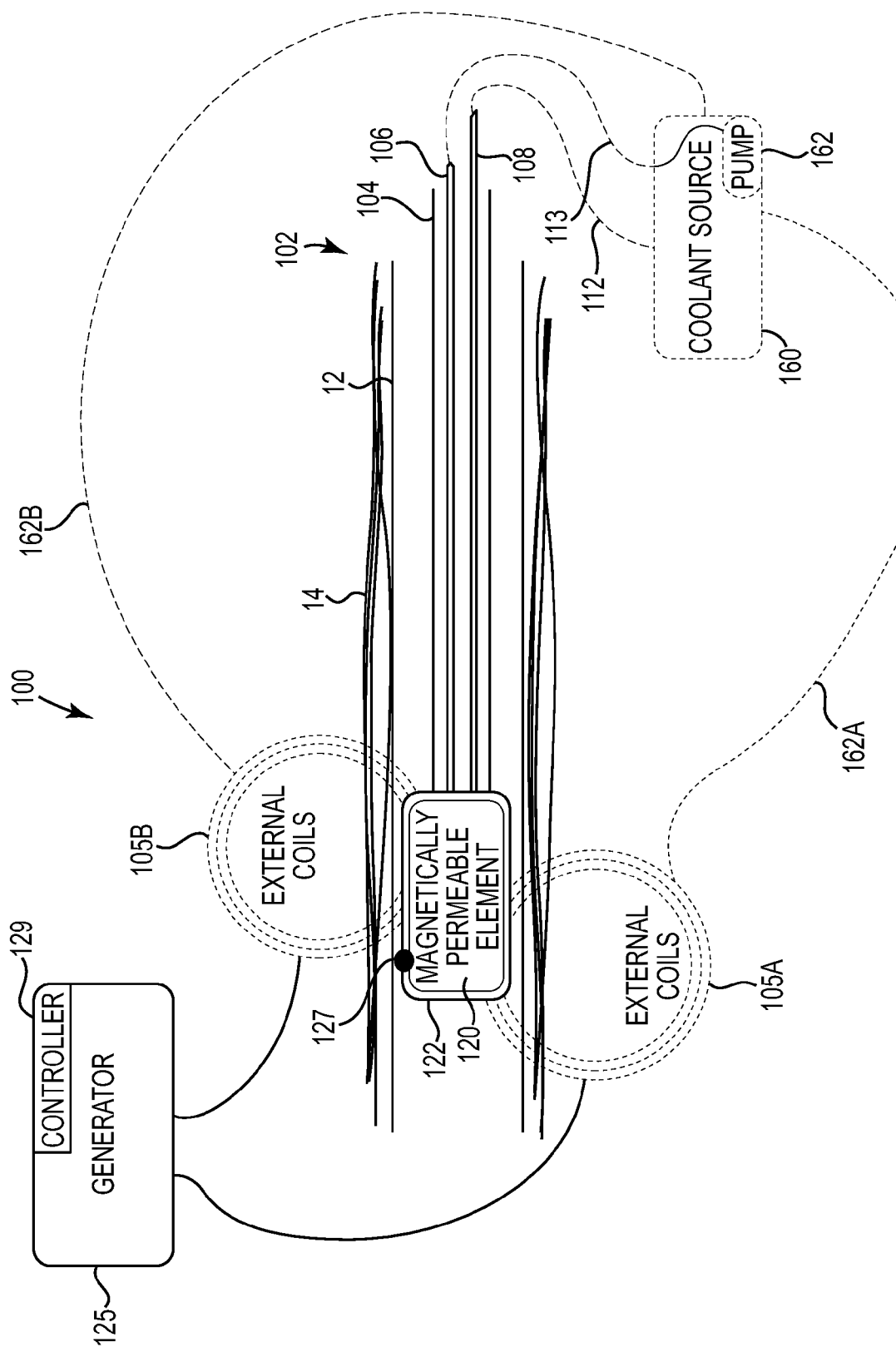
FIG. 6 illustrates an apparatus for producing ablative heating in innervated renal arterial and perivascular tissue provided from currents induced by an external magnetic field in accordance with various embodiments.

Turning now to FIG. 6, there is illustrated an apparatus 100 for producing ablative heating in innervated renal arterial and perivascular tissue provided from currents induced by an external magnetic field in accordance with various embodiments. In FIG. 6, the apparatus 100 includes a generator 125 electrically coupled to a pair of external coils 105A and 105B positioned on respective anterior and posterior portions of a patient in proximity to the renal artery 12. The external coils 105A and 105B may incorporate fluid channels or be thermally coupled to fluid channels for cooling the external coils 105A and 105B. The fluid channels of the external coils 105A and 105B are shown fluidly coupled to a coolant source 160 via lines 162A and 162B, respectively. Each of the coolant lines 162A and 162B preferably includes a supply line and a return line, with each of the supply lines fluidly coupled to a pump 162 of the coolant source 160.

FIG. 6 further shows a magnetic focusing catheter 102 which includes a magnetically permeable element 120. In some embodiments, the magnetically permeable element 120 is supported by, or contained within, a support arrangement 122 (e.g., balloon, vessel, tube). In embodiments that employ a balloon 122, an inflation lumen 106 is provided which extends along the length of the shaft 104 and is fluidly coupled to a pump 162 via a line 113. The support arrangement 122 is configured to position the magnetically permeable element 120 against the wall of the renal artery 12. The support arrangement 122 or other portion of the distal end of the shaft 104 preferably incorporates a perfusion or diversion apparatus to allow blood to flow through the renal artery 12 during the ablation procedure. In some embodiments, as previously discussed, the perfusion or diversion apparatus can be used to provide cooling to the renal artery wall during ablation.

In other embodiments, the support arrangement 122 or other structure at the distal end of the shaft 104 can be configured to receive a coolant or cryogen from an external coolant source 160 via a line 112 and a coolant lumen 108 of the shaft 104. For example, the support arrangement 122 can incorporate a cyroballoon or cryotube. A cryogen can be delivered from the coolant source 160 to the cyroballoon or cryotube of the support arrangement 122. In some implementations, a cryoballoon or cryotube can be configured to receive a liquid biocompatible cryogen, such as cold sterile saline or cold Ringer's solution, which is expelled into the blood flowing through the renal artery 12. In other implementations, the cryoballoon or cryotube can be constructed to provide phase-change cryothermal cooling by incorporating one or more orifices or narrowings to induce a phase change in a liquid cryogen supplied to the cryoballoon (e.g., Joule-Thomson cooling). Spent gas resulting from the phase change of the liquid cryogen is exhausted through an outlet fluidly coupled to an exhaust lumen extends to the proximal end of the catheter shaft 104. One or more temperature sensors 127 may be provided at the support arrangement 122 for measuring temperature approximating that of the renal artery wall adjacent the magnetically permeable element 120.

The generator 125 includes an oscillator configured to energize the external coils 105A and 105B to create a high-frequency oscillating magnetic field in body tissue between the external coils 105A and 105B including the renal artery 12 and perivascular renal nerve tissue proximate the renal artery 12. The generator 125 may include or be coupled to a controller 129 which controls the generator 125 in an automatic mode, semi-automatic mode or manual mode. The controller 129 is preferably coupled to one or more temperature sensors 127 which generate sensor signals indicative of the temperature at the renal artery wall adjacent the magnetically permeable element 120. The controller 129 can be programmed to automatically adjust the magnetic field produced between the external coils 105A and 105B based on the sensor signals received from the temperature sensors 127.

In general, when renal artery nerve tissue temperatures rise above about 113° F. (50° C.), protein is permanently damaged (including those of renal nerve fibers). If heated over about 65° C., collagen denatures and tissue shrinks. If heated over about 65° C. and up to 100° C., cell walls break and oil separates from water. Above about 100° C., tissue desiccates. According to some embodiments, the generator 125 is configured to control the magnetic field produced between the external coils 105A and 105B in response to signals received from temperature sensors 127 so that an intensified magnetic field created near the magnetically permeable element 120 causes heating of the perivascular renal nerve tissue 14 proximate the magnetically permeable element 120 to at least a temperature of 55° C.

Various embodiments disclosed herein are generally described in the context of ablation of perivascular renal nerves for control of hypertension. It is understood, however, that embodiments of the disclosure have applicability in other contexts, such as performing ablation from within other vessels of the body, including other arteries, veins, and vasculature (e.g., cardiac and urinary vasculature and vessels), and other tissues of the body, including various organs. Embodiments of the disclosure can be used for ablation of perivascular renal nerves, or for ablation of other tissues where a ferrofluid-filled catheter or elongated member or trocar can be placed for focusing the external magnetic field (e.g., diseased tissue, tumors, and organs). For example, for cardiac arrhythmia ablation, a catheter can be introduced through the vasculature and positioned in the left atrium. In another example, for treatment of BPH (benign prostatic hyperplasia), a catheter can be introduced through the urethra and positioned in the prostate.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A system, comprising:
an internal apparatus intended to be deployed within a patient, the internal apparatus including:
a flexible elongated member comprising a proximal end, a distal end, and a length sufficient to access a target vessel of the body relative to a percutaneous access location; and
a magnetically permeable element provided at a distal end of the elongated member, the magnetically permeable element having poor electrical conductivity and configured for placement within the target vessel and adjacent a wall of the target vessel; and
an external apparatus intended to be deployed outside of the patient, the external apparatus including:
one or more external coils positionable on one or both of anterior and posterior portions of a patient in proximity to the target vessel; and
a generator coupled to the external coils and configured to energize the external coils to create a high-frequency oscillating magnetic field in body tissue between the external coils including the target vessel and target tissue proximate the target vessel;
wherein the magnetically permeable element serves to concentrate the magnetic field, created by the external apparatus, in a region near the target vessel, the concentrated magnetic field inducing high frequency electric current sufficient to ablate the target tissue proximate the vessel.

2. The system of claim 1, wherein the magnetically permeable element comprises a vessel filled with fluid comprising magnetic material.

3. The system of claim 1, wherein the magnetically permeable element comprises a balloon, the balloon configured to receive a fluid comprising magnetic material.

4. The system of claim 1, wherein the magnetically permeable element comprises a balloon, the balloon formed from a composite material comprising magnetic material or comprising a coating of nonconductive or poorly conductive magnetic material.

5. The system of claim 1, wherein:
the magnetically permeable element comprises a balloon;
at least a circumferential region of the balloon is heated by the induced electric current; and
a complete circumferential region of the target tissue in proximity to the circumferential region of the balloon is ablated.

6. The system of claim 1, wherein the magnetically permeable element comprises a solid element or a coated element, the solid or coated element comprising nonconductive or poorly conductive magnetic material.

7. The system of claim 1, wherein the magnetically permeable element comprises a tube containing magnetic material.

8. The system of claim 1, wherein the magnetically permeable element comprises paramagnetic material and diamagnetic material arranged in geometries that enhance heating of the target tissue.

9. The system of claim 1, wherein the magnetically permeable element is configured to cooperate with an external bird cage coil that generates a rotating magnetic field, the magnetically permeable element configured to distort a magnetic field proximate the element so that time varying electric fields are produced that circulate in the target tissue at the rotation rate of rotating magnetic field.

10. The system of claim 1, further comprising a temperature sensor arranged to sense temperature proximate the magnetically permeable element.

11. The system of claim 1, further comprising a cooling arrangement at the distal end of the elongated member and configured to provide cooling to the target vessel during ablation of the target tissue.

12. The system of claim 1, wherein the magnetically permeable element is configured to create a circumferential lesion in the target tissue.

13. The system of claim 1, wherein the concentrated magnetic field is approximately 5-15 times greater than that in other regions of the body tissue between the external coils.

14. The system of claim 1, wherein the induced current causes local resistive heating near the magnetically permeable element approximately ≥100 times that in other areas of the body tissue subject to the magnetic field.

15. The system of claim 1, further comprising a cooling arrangement configured to cool the one or more external coils.

16. A system comprising:
a flexible elongated member comprising a proximal end, a distal end, and a length sufficient to access a renal artery relative to a percutaneous access location;
a magnetically permeable element provided at a distal end of the elongated member, the magnetically permeable element having poor electrical conductivity and configured for placement within the renal artery and adjacent a wall of the renal artery, the magnetically permeable element deployable within a patient;

one or more external coils positionable on one or both of anterior and posterior portions of the patient, exterior to the patient; in proximity to the renal artery; and a generator coupled to the external coils and configured to energize the external coils to create a high-frequency oscillating magnetic field in body tissue between the external coils including the renal artery and perivascular renal nerve tissue proximate the renal artery;

the magnetically permeable element serving to concentrate the magnetic field in a region near the renal artery, the concentrated magnetic field inducing high frequency electric current sufficient to ablate the perivascular renal nerve tissue proximate the renal artery.

17. The system of claim 16, further comprising a cooling arrangement at the distal end of the elongated member and configured to provide cooling to the renal artery during ablation of the perivascular renal nerve tissue.

18. The system of claim 16, further comprising a cooling arrangement configured to cool the one or more external coils.

19. The system of claim 16, wherein the magnetically permeable element is configured to create a circumferential lesion in the perivascular renal nerve tissue.

20. The system of claim 16, wherein:
the magnetically permeable element comprises a balloon; and
the balloon comprises a cooling arrangement configured to provide cooling to the renal artery during ablation of the perivascular renal nerve tissue.

21. A method, comprising:
energizing one or more external coils positionable on one or both of anterior and posterior portions of a patient in proximity to a renal artery to create a high-frequency oscillating magnetic field in body tissue between the external coils including renal artery tissue and perivascular renal nerve tissue adjacent the renal artery;

concentrating the magnetic field in a region near the renal artery; and ablating the perivascular renal nerve tissue using high frequency electric current induced in the perivascular renal nerve tissue by the concentrated magnetic field.

22. The method of claim 21, wherein:
concentrating the magnetic field comprises concentrating the magnetic field in a region near a magnetically permeable element situated in the renal artery; and
ablating the perivascular renal nerve tissue comprises ablating the perivascular renal nerve tissue using high frequency electric current induced in the perivascular renal nerve tissue proximate the magnetically permeable element by the concentrated magnetic field.

23. The method of claim 21, further comprising providing cooling to the renal artery during ablation of the perivascular renal nerve tissue.

* * * * *